US012508370B2

(12) United States Patent

Boström

(10) Patent No.: US 12,508,370 B2
(45) Date of Patent: Dec. 30, 2025

(54) SUB-ASSEMBLY FOR MEDICAMENT DELIVERY DEVICE, AND MEDICAMENT DELIVERY DEVICE COMPRISING THE SUB-ASSEMBLY

(71) Applicant: SHL MEDICAL AG, Zug (CH)

(72) Inventor: Anders Boström, Ingarö (SE)

(73) Assignee: SHL Medical AG, Zug (CH)

( * ) Notice: Subject to any disclaimer, the term of this patent is extended or adjusted under 35 U.S.C. 154(b) by 749 days.

(21) Appl. No.: 17/796,100

(22) PCT Filed: Nov. 12, 2020

(86) PCT No.: PCT/EP2020/081839

§ 371 (c)(1),
(2) Date: Jul. 28, 2022

(87) PCT Pub. No.: WO2021/170263

PCT Pub. Date: Sep. 2, 2021

(65) Prior Publication Data

US 2023/0338662 A1 Oct. 26, 2023

(30) Foreign Application Priority Data

Feb. 24, 2020 (EP) .................................... 20158981

(51) Int. Cl.

*A61M 5/315* (2006.01)
*A61M 5/20* (2006.01)
*A61M 5/32* (2006.01)

(52) U.S. Cl.

CPC ...... *A61M 5/31501* (2013.01); *A61M 5/2033* (2013.01); *A61M 5/3202* (2013.01); *A61M 2005/2013* (2013.01)

(58) Field of Classification Search

CPC ............ A61M 5/2033; A61M 5/31501; A61M 5/3202; A61M 2005/2013
See application file for complete search history.

(56) References Cited

U.S. PATENT DOCUMENTS

2018/0104414 A1* 4/2018 Karlsson ............. A61M 5/2033

FOREIGN PATENT DOCUMENTS

WO 2011/123024 A1 10/2011
WO 2016/128207 A1 8/2016
(Continued)

OTHER PUBLICATIONS

International Search Report and Written Opinion for Int. App. No. PCT/EP2020/081839, mailed Nov. 26, 2020.

*Primary Examiner* — John Kim
(74) *Attorney, Agent, or Firm* — McDonnell Boehnen Hulbert & Berghoff LLP

(57) ABSTRACT

The present disclosure relates to a sub-assembly for medicament delivery device, which has an engageable releasing means, and a medicament delivery device including the sub-assembly. The engageable releasing means provides force for injecting medicament contained in the device when the engageable releasing means is released. For a conventional sub-assembly having an engageable releasing means, there is high possibility that the engageable releasing means is released during transportation of the sub-assembly to a final assembly location. To address this problem, particularly caused by unintentional external axial forces applied to the sub-assembly during transportation, the present disclosure applies a coupling mechanism to securely hold in an axial direction components including the engageable releasing means. Therefore, the sub-assembly and the medicament delivery device according to the present disclosure can prevent unintentional release of the engageable releasing means reliably.

15 Claims, 9 Drawing Sheets

(56) References Cited

FOREIGN PATENT DOCUMENTS

| | | | |
|---|---|---|---|
| WO | 2016/169748 | A1 | 10/2016 |
| WO | 2019/137701 | A1 | 7/2019 |
| WO | 2020/015984 | A2 | 1/2020 |

* cited by examiner

Fig. 1- Prior Art
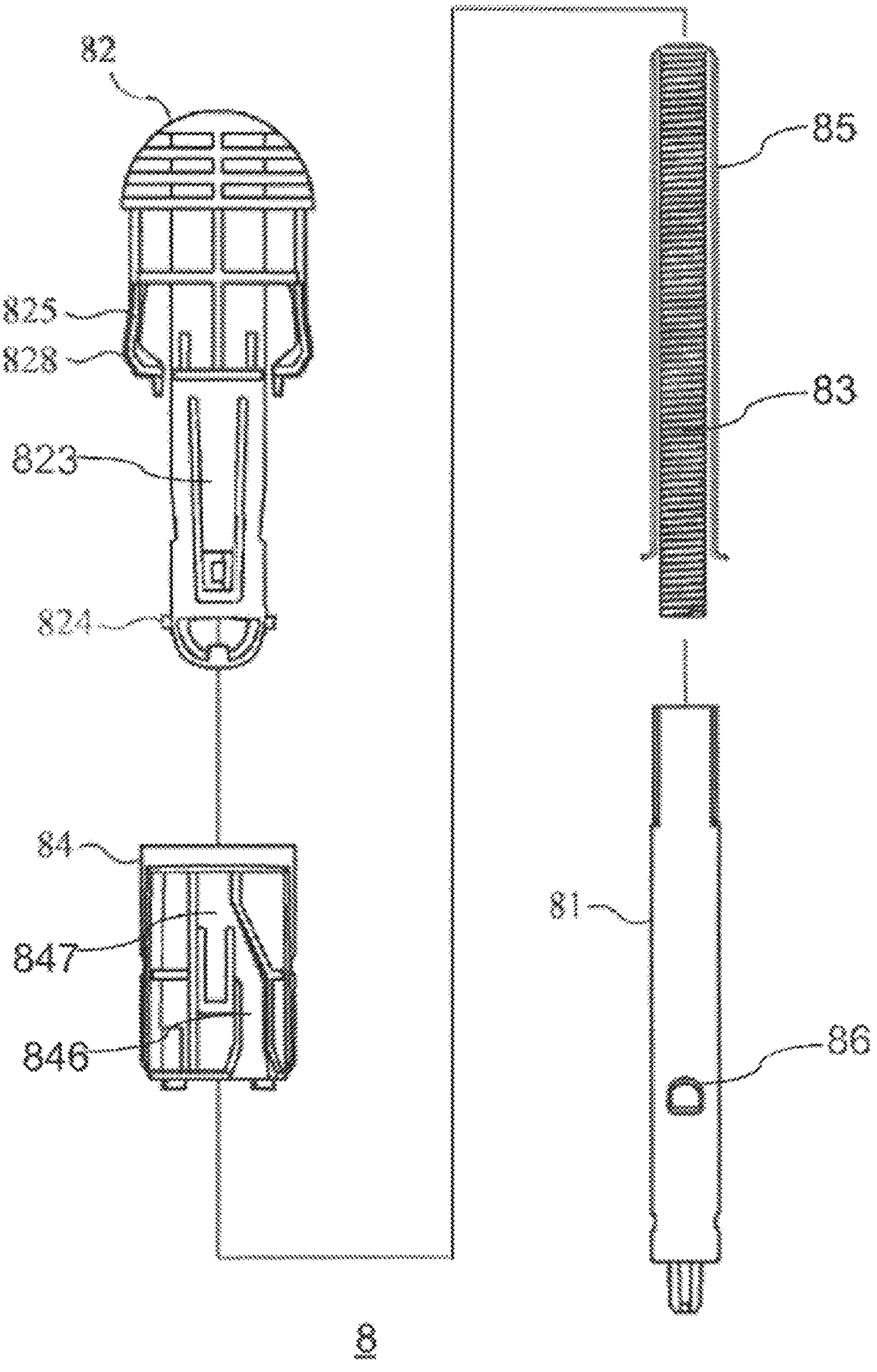

Fig. 2A - Prior Art
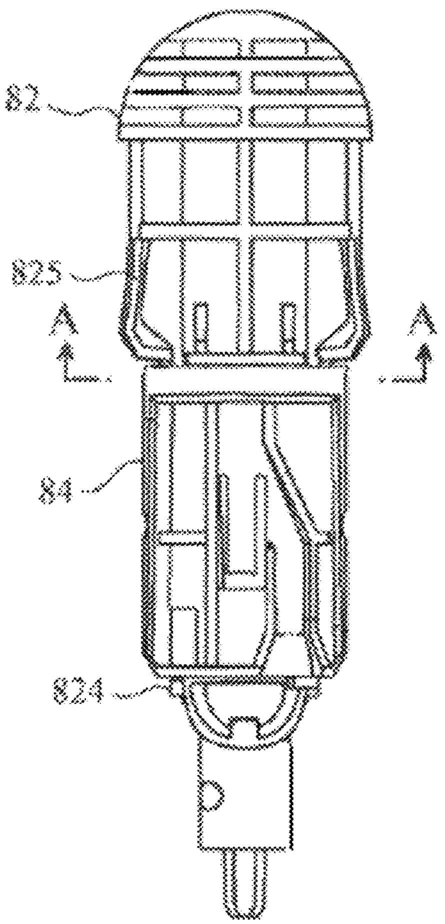
Fig. 3A- Prior Art
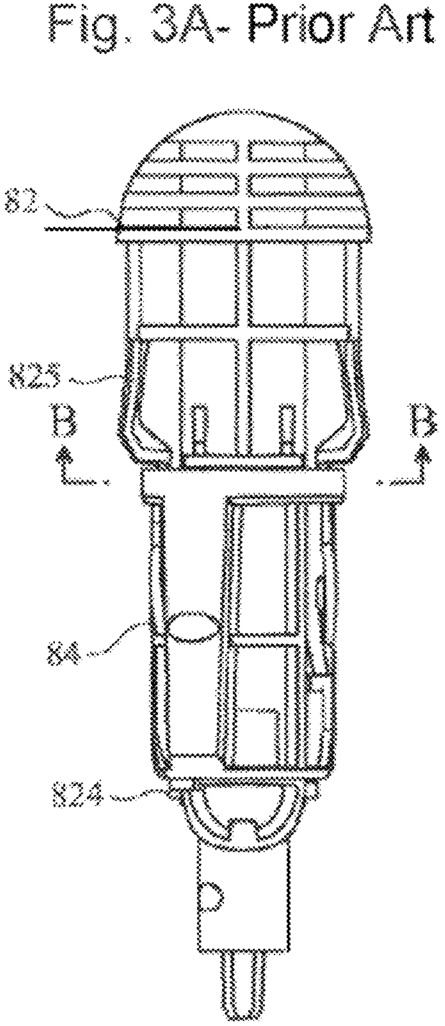
Fig. 2B- Prior Art
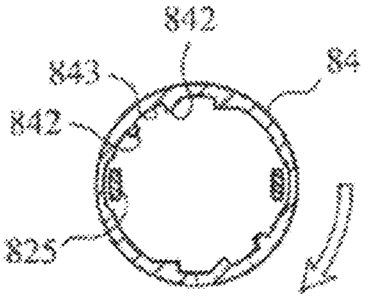
Fig. 3B - Prior Art
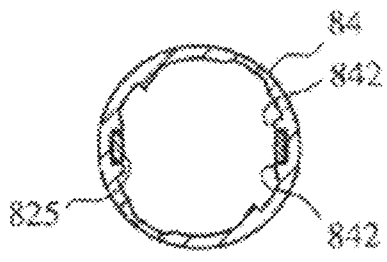

Fig. 4 - Prior Art
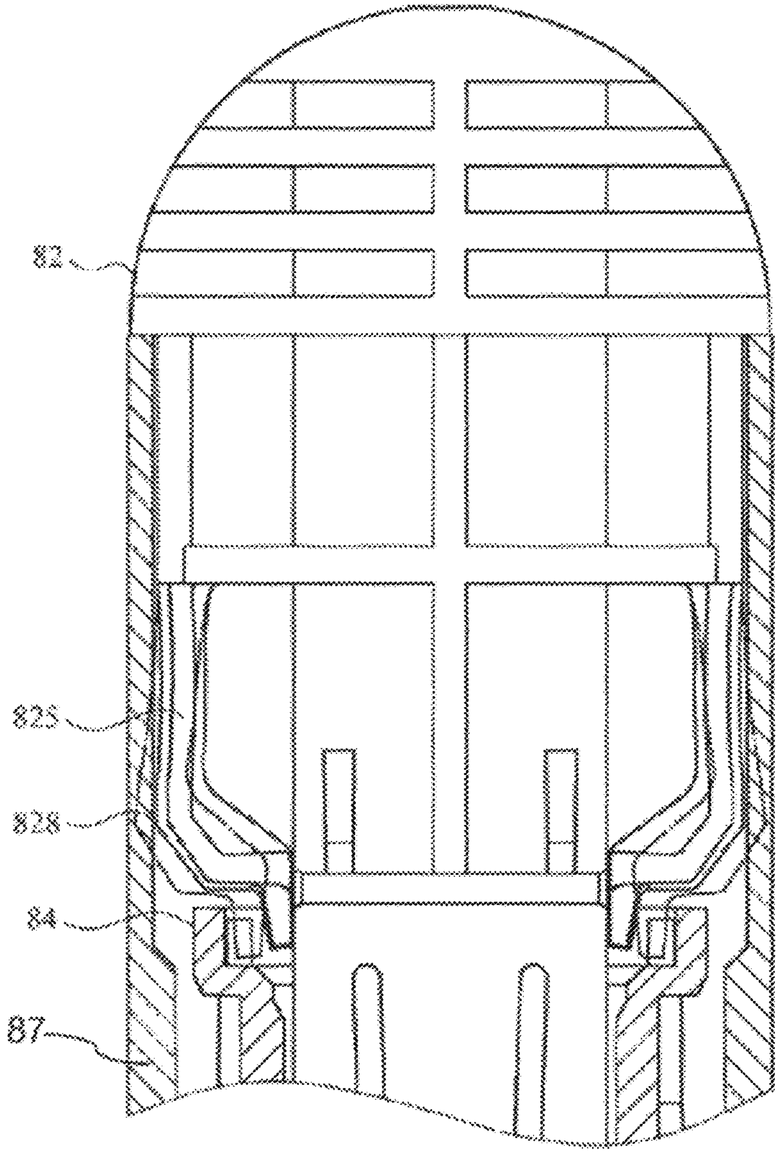

SUB-ASSEMBLY FOR MEDICAMENT DELIVERY DEVICE, AND MEDICAMENT DELIVERY DEVICE COMPRISING THE SUB-ASSEMBLY

CROSS REFERENCE TO RELATED APPLICATIONS

The present application is a U.S. National Phase Application pursuant to 35 U.S.C. § 371 of International Application No. PCT/EP2020/081839 filed Nov. 12, 2020, which claims priority to European Patent Application No. 20158981.9 filed Feb. 24, 2020. The entire disclosure contents of these applications are herewith incorporated by reference into the present application.

TECHNICAL FIELD

The present disclosure generally relates to a sub-assembly of medicament delivery device comprising a transportation locking mechanism, and a medicament delivery device comprising the sub-assembly.

BACKGROUND

Many medicament delivery devices have been developed for users to perform the medicament delivery on their own. Document WO 2011/123024 (referred as "WO '024" in the following) and WO 2016/169748 (referred as "WO '748" in the following) disclose such medicament delivery devices.

A medicament delivery device and a sub-assembly for the device according to WO '748 was proposed to resolve the problem that a delivery actuation means included in the sub-assembly of medicament delivery device according to WO '024 is actuated while the sub-assembly is being transported for the final assembly. Specifically, a plunger rod in WO '024 may be catapulted by disengagement between a recess on the plunger rod and a protrusion engaged with the recess during transportation (see FIGS. 4C and 5 of WO '024). This disengagement may be caused by force unintentionally applied to the sub-assembly during transportation.

FIGS. 1 to 4 show a sub-assembly 8 including a delivery actuation means according to WO '748. Key structural elements in WO '748 for preventing the unintentional catapulting of the plunger rod are flexible tabs 825 oppositely arranged in a main body 82, and recesses 843 and protrusions 842 formed on an inner surface of a coupling member 84.

Each flexible tab 825 has a cantilever structure. One end of the flexible tab 825 is fixed to the main body 82, and the other end is a free end. A proximal half of the tab 825 extends radially outwards from the longitudinal axis of the main body 82, and then extends radially inwards to form an arch 828. A distance between the arch 828 and the central axis of the main body 82 is larger than a distance between other portions of the tab 825 and the central axis, than an outer radius of the coupling member 84, and also than an inner radius of a housing 87 into which the sub-assembly is inserted for the final assembly of the medicament delivery device.

When the coupling member 84 is mounted on and then rotated relative to the main body 82, the free end of the tab 825 snaps into the recess 843 along with being bent radially inwards. In this coupling state, due to the engagement between the free end of the flexible tab 825 and the recess 843, the coupling member 84 is prevented from rotating relative to the main body 82. Since the coupling member 84 is rotationally locked to the main body 82, a flexible arm 823 can be confined by the coupling member 84, and the free end of the flexible arm 823 can maintain the state of locking a plunger rod 81 by being engaged with an engagement hole 86 on the plunger rod 81.

After transportation, the sub-assembly 8 is assembled with other sub-assemblies to form the final assembly of the medicament delivery device. In the final assembly, most parts of the sub-assembly 8 are inserted into a housing 87. As shown in FIG. 4, an inner surface of the housing 87 bends the flexible tab 825 radially inwards to the extent that the free end of the flexible tab 825 is totally released from the recess 843. Therefore, the coupling member 84 becomes ready to be rotated by interactions between rotation guides 846, 847 formed on an outer surface of the coupling member 84, and protrusions (not shown) formed on an element moving linearly along the housing 87 when the medicament delivery device is in the injection state.

As discussed above, the coupling member 84 is rotationally locked to the main body 82 by the engagement between the flexible tab 825 and the recess 843. However, the coupling member 84 may be still moveable relative to the main body 82 in the longitudinal direction of the main body 82. Therefore, when an unintentional external axial force is applied to the coupling member 84, the coupling member 84 may be axially dislocated from its original position relative to the main body 82, and consequently the plunger rod 81 may be catapulted by disengagement between the engagement hole 86 and the free end of the flexible arm 823.

To prevent this axial dislocation of the coupling member 84, there are provided at least one protrusion 824 at a proximal end portion of the main body 82. After the main body 82 is fully inserted into the coupling member 84 up to a predetermined position, the protrusions 824 are positioned to restrict a proximal movement of the coupling member 84 relative to the main body 82, and thus ensure maintaining the engagement between the free end of the flexible tab 825 and the recess 843 in the distal end portion of the coupling member 84.

However, the inventor of the present disclosure found that the protrusions 824 are under the risk of breakage or wear, and may cause failure on the delivery of medicament. This breakage or wear of the protrusions 824 arises from interference of the protrusions 824 with the coupling member 84 and/or a U-bracket 85.

The protrusions 824 continuously exert forces on the coupling member 84 to restrict the axial movement of the coupling member 84. In cases where a big external force is applied to the coupling member 84 and/or the main body 82, a portion of the protrusions 824 may break.

The sub-assembly 8 contains the U-bracket 85 which supports an end of a resilient member 83 and is inserted into the main body 82 together with the resilient member 83 and the plunger rod 81. End tips of the U-bracket are seated adjacent to or on the protrusions 824. Since the U-bracket 85 is made of metal and the main body 82 is made of plastic material, movement of the end tips of the U-bracket in relation to the protrusions 824 may damage the protrusions 824 while generating plastic particles from the protrusions 824.

SUMMARY

The following description and drawings disclose embodiments of the present disclosure and their implementation variants. The scope of protection is defined by the claims, to which reference should now be made.

In the present disclosure, when the term “distal” is used, this refers to the direction pointing away from a dose delivery site where a dose of medicament is delivered. When the term “distal part/end” is used, this refers to the part/end of the delivery device, or the parts/ends of the members thereof, which under use of the medicament delivery device is/are located furthest away from the dose delivery site. Correspondingly, when the term “proximal” is used, this refers to the direction pointing to the dose delivery site. When the term “proximal part/end” is used, this refers to the part/end of the delivery device, or the parts/ends of the members thereof, which under use of the medicament delivery device is/are located closest to the dose delivery site.

Further, the term “longitudinal”, with or without “axis”, refers to a direction or an axis through the device or components thereof in the direction of the longest extension of the device or the component. In a similar manner, the terms “radial” or “transversal”, with or without “axis”, refers to a direction or an axis through the device or components thereof in a direction generally perpendicular to the longitudinal direction. For instance, the term “radially outward” would refer to a direction pointing away from the longitudinal axis.

References to a ‘height difference’ in this application mean a difference in distance from a central axis running in a longitudinal direction through the sub-assembly or through the device.

According to the disclosure in the present description and drawings, there is provided a sub-assembly for a medicament delivery device, comprising: a plunger rod; a biasing member configured to bias the plunger rod; a tubular main body comprising a hollow cylinder, wherein the plunger rod and the biasing member are in the hollow cylinder, the main body comprising a holding member attached to the hollow cylinder; and a tubular coupling member arranged to be rotatable relative to the main body. The holding means is configured to have, at least, a holding position in which the holding member is engaged with the plunger rod, and a releasing position in which the holding member is released from the plunger rod, the holding member being switchable from the holding position to the releasing position depending on rotational positions of the coupling member relative to the main body. The main body comprises a first axial engagement element formed on an outer surface of the hollow cylinder; and the coupling member comprises a second axial engagement element formed on an inner surface of the coupling member. The main body and the coupling member are configured such that the first and second axial engagement elements are engaged with each other to restrict a movement of the coupling member relative to the main body in a proximal direction. This can enable a pre-determined relative position between the coupling member and the main body to be maintained reliably even in cases where significant external forces are applied to the sub-assembly during transportation. It can also prevent generation of plastic particles from the protrusions on the main body, such that the possibility of operation failure of the medicament delivery device due to plastic debris can be reduced.

Preferably, the first axial engagement element may be arranged to protrude radially outwards from the outer surface of the hollow cylinder.

Preferably, the second axial engagement element may be arranged to protrude radially inwards from the inner surface of the coupling member.

Preferably, the holding member may have one end which is connected to the hollow cylinder, and the other end which is a free end and capable of being engaged with the plunger rod.

Preferably, the first axial engagement element may be disposed on an outer surface of the holding member.

Preferably, the first axial engagement element may be arranged to protrude radially outwards from the outer surface of the hollow cylinder; and the second axial engagement element may comprise a groove which is formed on the inner surface of the coupling member and capable of being engaged with the first axial engagement element.

Preferably, the first axial engagement element may comprise a groove which is formed on the outer surface of the hollow cylinder; and the second axial engagement element may be arranged to protrude radially inwards from the inner surface of the coupling member. The groove of the first axial engagement element is capable of being engaged with the second axial engagement element.

Preferably, the groove may be formed to extend along a circumferential direction of the coupling member or the hollow cylinder, such that the engagement between the first and second engagement elements via the groove may be maintained when the coupling member is rotated relative to the main body to a certain degree.

Preferably, the second axial engagement element may be disposed between the proximal and distal ends of the coupling member.

Preferably, the coupling member may further comprise a proximal surface which is disposed more proximally than the second axial engagement element.

Preferably, the proximal surface may have a height difference from the second axial engagement element.

Preferably, the proximal surface may have a step with respect to the second axial engagement element.

Preferably, the proximal surface may be arranged to abut the first axial engagement element.

Preferably, the coupling member may have a releasing rotational position and a holding rotational position, relative to the main body.

Preferably, the releasing rotational position and the holding rotational position may respectively correspond to the releasing position and the holding position of the holding member.

Preferably, the first and second axial engagement elements may be engaged with each other when the coupling member is in the holding rotational position.

Preferably, the coupling member may comprise a central through-hole into which the main body can be inserted, and a longitudinal groove which can guide insertion of the main body into the coupling member.

Preferably, the coupling member may be rotatable relative to the main body when the main body is inserted into the coupling member along the longitudinal groove up to a pre-determined fully-inserted position.

Preferably, the coupling member may be in the releasing rotational position when the main body is inserted into the coupling member up to the pre-determined fully-inserted position.

Preferably, the coupling member may be in the holding rotational position when the coupling member is rotated in a first rotational direction by a pre-set angle from the pre-determined fully-inserted position.

Preferably, the first and second axial engagement elements become engaged with each other when an external force is applied to the sub-assembly after the coupling member is rotated by said pre-set angle relative to the main body.

Preferably, the first and second axial engagement elements may be engaged with each other via the groove, when the position of the coupling member is changed from the releasing rotation position to the holding rotational position, or when an external force is applied to the sub-assembly after the coupling member is rotated by said pre-set angle relative to the main body.

The present description further discloses a medicament delivery device such as an autoinjector, the medicament delivery device comprising a sub-assembly as described above. Preferably, the medicament delivery device comprises: a housing; an activation member disposed in the housing and linearly movable along the longitudinal direction of the housing; a medicament container disposed inside the activation member, containing medicament, and comprising a slidable stopper arranged to expel the medicament out of the medicament container, and medicament delivery member such as a needle connected with a proximal end portion of the medicament container; a resilient member arranged to apply force to move the activation member in the proximal direction of the medicament delivery device; and the sub-assembly of any one of the preceding claims, which is coupled to the distal end of the housing, arranged to push the slidable stopper when the plunger rod is released, and comprises a means of restricting a second movement of the activation member in the distal direction of the medicament delivery device after the activation member has moved in the distal direction.

The medicament delivery device may be an injection device.

BRIEF DESCRIPTION OF THE DRAWINGS

The accompanying drawings, which are included to provide a further understanding of the present disclosure and constitute a portion of the specification, illustrate embodiments of the present disclosure, and together with the description serve to explain the principle of the present disclosure.

FIG. 1 is an exploded plain view of a sub-assembly disclosed in WO '748.

FIG. 2A is an assembled plain view of the sub-assembly of FIG. 1 illustrating a state that the coupling member 84 is not locked by the flexible tab 825;

FIG. 2B is a sectional view of FIG. 2A taken along a line A-A;

FIG. 3A is an assembled plain view of the sub-assembly of FIG. 1 illustrating a state that the coupling member 84 is locked by the flexible tab 825;

FIG. 3B is a sectional view of FIG. 3A taken along a line B-B;

FIG. 4 is a partially enlarged sectional view illustrating different positions of the flexible tab 825 when the sub-assembly of FIG. 1 is inserted into the housing 87 for the final assembly of the medicament delivery device;

DETAILED DESCRIPTION

Figure 5:
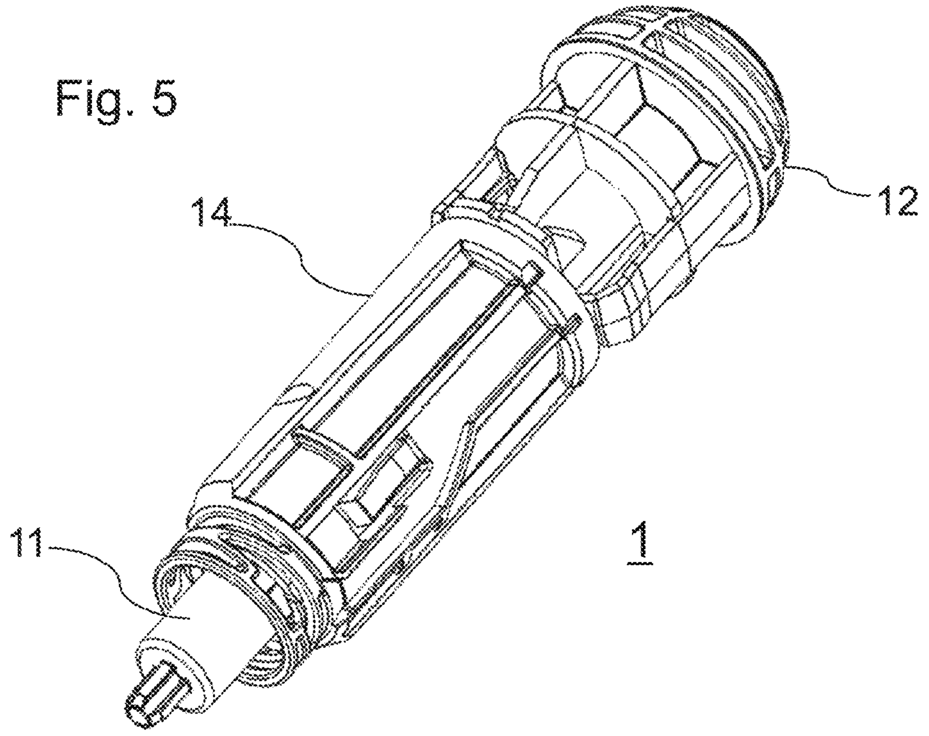
FIG. 5 is an assembled perspective view of a sub-assembly according to an embodiment of the present disclosure.
Figure 6:
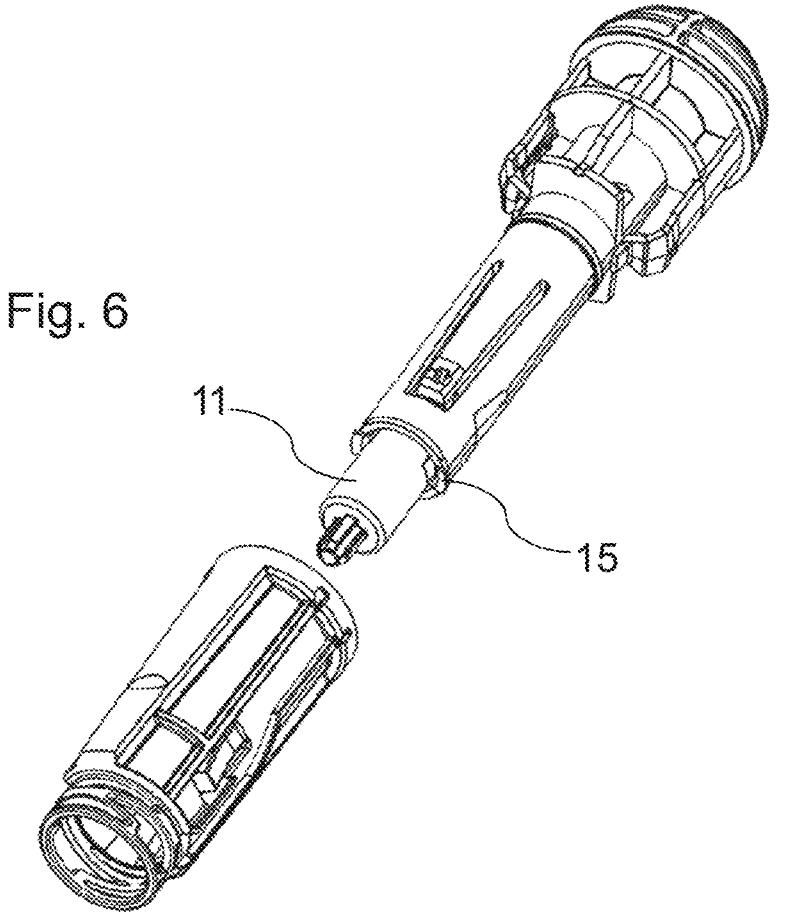
FIG. 6 is an exploded perspective view of a sub-assembly according to the embodiment of the present disclosure.
Figure 7:
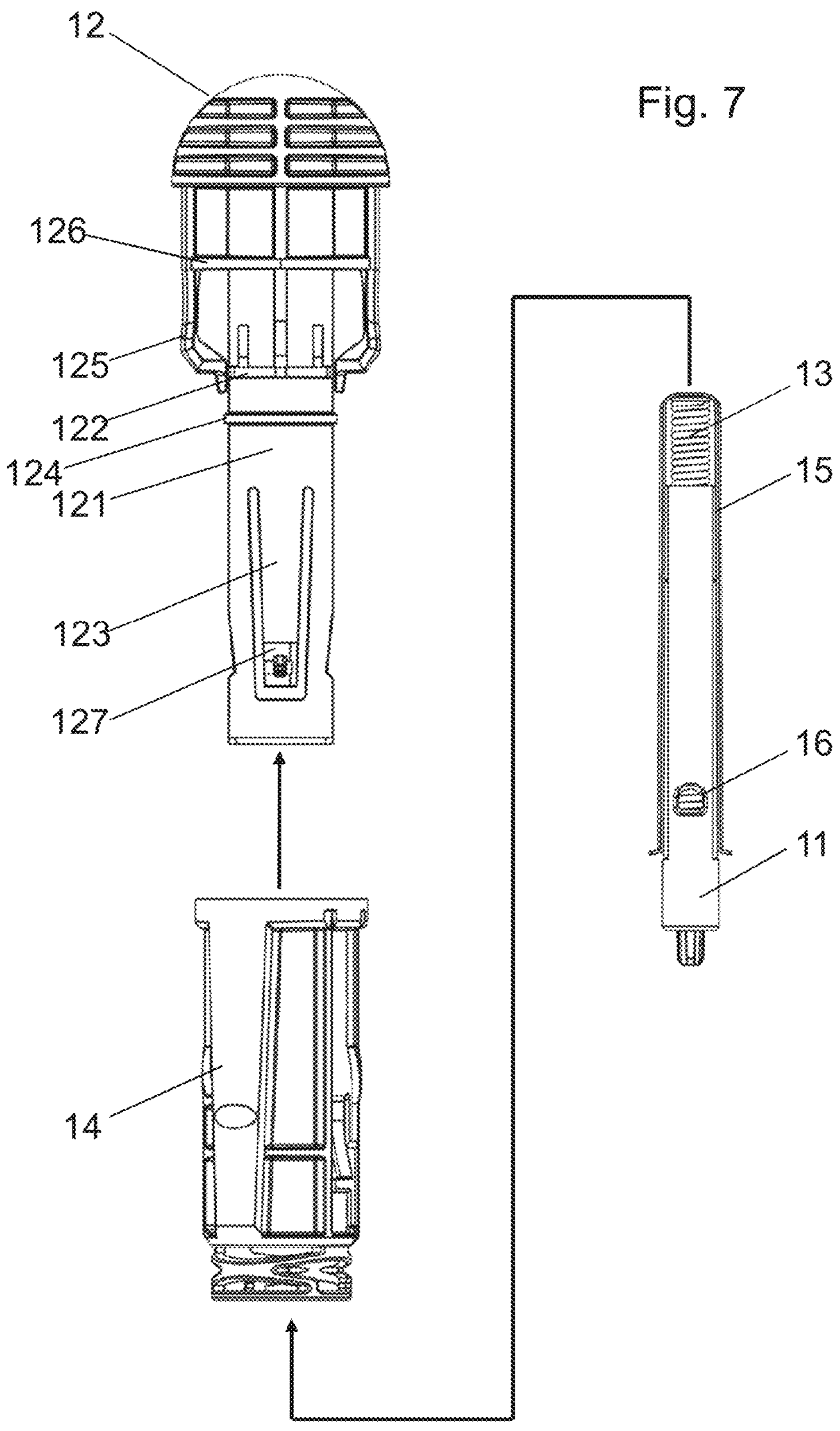
FIG. 7 is an exploded plain view of the sub-assembly according to the embodiment of the present disclosure.

FIGS. 5 to 10C show a sub-assembly 1 of medicament delivery device according to an embodiment of the present disclosure.

The sub-assembly 1 comprises a plunger rod 11 having an engagement hole 16, a main body 12 which slidably receives the plunger rod 11, a biasing member 13 which is accommodated in the plunger rod 11 for biasing the plunger rod 11, and a coupling member 14 arranged to be rotationally moveable relative to the main body 12. The biasing member 13 may be a tension spring, but is not limited to this. A U-bracket 15 may be further installed to partially enclose the biasing member 13 and the plunger rod 11. The U-bracket 15 guides the releasing motion of the plunger rod 11 and the biasing member 13.

The main body 12 comprises a hollow cylinder 121. A rib 122 may be arranged to radially extend from the cylinder 121 and divides the hollow cylinder 121 into a proximal section and a distal section. A holding means 123 is formed in the proximal section of the main body 12. The holding means 123 constitutes a portion of the hollow cylinder 121. The figures show a flexible arm on the cylinder 121 as such holding means 123, but the disclosure is not limited to this specific type. The holding means 123 may have a free end. An end tip of the holding means 123 at the free end is configured to be engaged with the plunger rod 11 to hold the biased plunger rod 11 until the medicament delivery device is activated. The free end of the holding means 123 is formed to be positioned radially more outwards than a proximal end portion of the hollow cylinder 121, before the main body 12 is assembled with the coupling member 14. Thus, the holding means 123 can be used to determine an angular position of the main body 12 relative to the coupling member 14, when the main body 12 and the coupling member 14 are assembled together.

A first axial engagement element 127 is formed to protrude radially outwards from an outer surface of the holding means 123. The first axial engagement element 127 works for restricting the movement of the coupling member 14 relative to the main body 12 in the proximal direction, by engagement with a second axial engagement element 144*a* formed on the coupling member 14. The first axial engagement element 127 may include a step having a height difference from the other outer surface of the holding means 123.

At least one first radial engagement element 125 is formed to extend proximally from the distal section. The main body 12 has two first radial engagement elements 125 which are oppositely arranged relative to the longitudinal axis. A radial wall 126 extends radially outward from the cylinder 121 and abuts a distal portion of the first radial engagement element 125 to radially support the first radial engagement element 125. The structure of the first radial engagement element 125 is similar to the structure of the flexible tab 825 in WO '748. In comparison with the main body 82 in WO '748, the main body 12 of the present disclosure does not have protrusions formed on the outer surface of the hollow cylinder 121, which corresponds to the protrusion 824. An optional ridge 124 is provided on the cylinder 121, extending around the cylinder (see FIG. 7 in particular) between the radial wall 126 and the holding means 123. The ridge 124 can help stabilise the rotator and can help avoid wobbling during activation.

The coupling member 14 has a hollow cylindrical shape. The coupling member 14 may include a central through-hole 140 into which the main body 12 can be inserted. The coupling member 14 may include a bore at the distal end of the coupling member 14. Thus, the bore forms a part of the central through-hole 140. The bore is surrounded by a rim 145 having an inner diameter larger than diameters of the other parts of the central through-hole.

A longitudinal groove 141 may be formed on an inner surface of the coupling member 14. The second axial engagement element 144*a* may be formed on an inner surface of the coupling member 14. The inner surface on which the second axial engagement element 144*a* is formed may be located more inward than the inner surface on which the longitudinal groove 141 is formed. The second axial engagement element 144*a* may be located adjacent to the longitudinal groove 141. The second axial engagement element 144*a* may be located apart from the proximal end and/or the distal end of the coupling member 14. There may be provided with a proximal inner surface 144*b*, which is located more proximally than the second axial engagement element 144*a*. In a normal state where the coupling member 14 and the main body 12 are assembled together and the plunger rod 11 is held by the holding means 123, the proximal inner surface 144*b* contacts an end portion of the holding means 123 and allows the end tip 123*b* of the hold means 123 to move radially inwards and thus to be engaged with an engagement hole 16 of the plunger rod 11. In a state where the assembled coupling member 14 and main body 12 undergo external axial forces, the first and second axial engagement elements 127 and 114*a* are engaged with each other, such that this engagement keeps the coupling member 14 and the main body 12 from relatively moving in the longitudinal direction and thus being disassembled.

At least two protrusions 142*a*, 142*b* are formed to extend radially inwards from an inner surface of the rim 145 at the distal end of the coupling member 14. A recess 143 may be formed between adjacent protrusions 142*a*, 142*b*. Each of the protrusions 142*a*, 142*b* may have a ramp-shaped first surface extending inwards from the inner surface of the rim 145 and a wall-shaped second surface extending substantially orthogonally from the inner surface of the rim 145. Alternatively, only one of the protrusions 142*a* may have such a first ramp-shaped surface and a second wall-shaped surface. The other protrusion 142*b* may have two wall-shaped surfaces.

A ramp-shaped surface of one of the protrusions 142*a*, 142*b* may guide the first radial engagement elements 125 to move radially inwards while the coupling member 14 is being rotated relative to the main body. A wall-shaped surface of one of the protrusions 142*a*, 142*b* may restrict a rotational movement of the end portion of the first radial engagement elements 125 while the coupling member 14 is rotated relative to the main body.

The coupling member 14 is mounted on the main body 12 by the main body 12 being inserted into the central through-hole of the coupling member 14. In order for the main body 12 to be inserted into the central through-hole of the coupling member 14, the longitudinal groove 141 of the coupling member 14 and the holding means 123 have to be angularly aligned first. After this alignment is made, the coupling member 14 can slide on the outer surface of the hollow cylinder 121.

When the main body 12 reaches a pre-determined fully-inserted position, an end portion of the first radial engagement element 125 is positioned in the recess 143. Then, the coupling member 14 is rotated in the counterclockwise direction (referred to in FIG. 8) at said pre-determined fully-inserted position of the main body 12. The end portion of the first radial engagement element 125 moves along the ramp-shaped first surface of the protrusion 142*a* and then is seated on the recess 143. Due to this coupling between the end portion of the first radial engagement element 125 and the recess 142, the rotational movement of the coupling member 14 caused by unintentional external forces can be prevented.

By the way, when the coupling member 14 starts to be rotated in the counterclockwise direction (referred to in FIG. 8) after the main body 12 is inserted into the coupling member 14 up to the pre-determined axial position, an inner edge of the longitudinal groove 141 interferes with a chamfered edge 123*a* of the holding means 123. By further rotation of the coupling member 14, the proximal inner surface 144*b* of the coupling member 14 rides upon the holding means 123 and allows the end tip of the holding means 123 to move radially inwards. After that, when a sub-assembly consisting of the biasing member 13, the plunger rod 11 and the U-bracket 15 is inserted into the cylinder 121 of the main body 12, the inward-moved end tip of the holding means 123 can be engaged with the engagement hole 16 and thus hold the plunger rod 11 until being released for injection of medicament.

There is a first radial height difference, i.e. a first step, between the proximal inner surface 144*b* and the second axial engagement element 144*a*. There is a second radial height difference, i.e. a second step, between the first axial engagement element 127 and the other outer surface of the holding means 123. The first axial engagement element 127 of the holding means 123 is seated on the proximal inner surface 144*b* after the coupling member 14 has been rotated in said counterclockwise direction. When an unintentional external axial force is applied to the coupling member 14 and/or the main body, and the coupling member 14 is about to move in the proximal direction, the first and second axial engagement elements 127 and 144*a* are engaged with each other by interference between said first and second steps. This engagement thus prevents the coupling member 14 and the main body 12 from being displaced from their pre-set relative axial positions, and thus disassembled from each other.

On the other hand, the holding means 123 has two positions. The first one is a holding position, in which the holding means 123 is engaged with the plunger rod 11, and which is provided when the coupling member 14 is at a first rotational position (referred to as "a holding rotational position") relative to the main body 12. The second one is a releasing position, in which the holding means (flexible arm) 123 is not engaged with the plunger rod 11, and which is provided when the coupling member 14 is at a second rotational position (referred to as "a releasing rotational position") relative to the main body 12. The first and second rotational positions are different from each other.

At the moment when the main body 12 is inserted into the coupling member 14 straight along the longitudinal groove 141 up to the pre-determined fully-inserted position, the holding means 123 may be in the releasing position. At the moment when the proximal inner surface 144*b* of the coupling member 14 rides on the holding means 123 after the relative counterclockwise rotation of the coupling member 1, the holding means 123 may be in the holding position. The first axial engagement element 127 may abut the proximal inner surface 144*b* when the holding means 123 is in the holding position.

According to the present disclosure, any structural element corresponding to the projection 824 on the main body 82 in WO '748 can be removed, since the function of the projection 824, which restricts the movement of the coupling member 84 in the proximal direction, is performed by the engagement between the first and second axial engagement elements 127, 144*a*.

The present disclosure can be implemented by embodiments other than, or variants of, the above-described embodiment.

In a variant (not illustrated), the first axial engagement element 127 may not be formed on the holding means 123. Any structural element which is connected to the hollow cylinder 121 of the main body 12, may be able to provide a place on which the first axial engagement element 127 is installed.

In another variant (not illustrated), the first axial engagement element 127 may have at least a portion protruding from the other portions thereof. Further, the first axial engagement element 127 may have a form of a step or a tooth.

In another variant (not illustrated), the first axial engagement element 127 may comprise a protrusion formed on the outer surface of the cylinder 121, and the second axial engagement element 144*a* may comprise a groove capable of being engaged with said protrusion and formed on an inner surface of the coupling member 14. The groove may be extended along a circumferential direction of the coupling member 14, such that the engagement between said protrusion and the groove may be maintained even when the coupling member 14 is further rotated relative to the main body 12. The groove may have a height difference from the proximal inner surface 144*b* or another surface of the second axial engagement element 144*a*. The engagement between said protrusion and the groove may be made immediately when the coupling member 14 is rotated in counterclockwise after the main body 12 has been inserted in the coupling member 14 up to the pre-determined fully-inserted position. Alternatively, this engagement may be made when the coupling member 14 is slightly moved in the proximal direction relative to the main body 12 after said counterclockwise rotation of the coupling member 14.

In another variant (not illustrated), the protrusion and the groove described in the above variant may be formed in the other way around. That is, the protrusion may be formed on the inner surface of the coupling member 14, and the groove capable of being engaged with said protrusion may be formed on the outer surface of the cylinder 121.

In the above variants involving the groove for the engagement between the first and second axial engagement elements 127, 144*a*, a portion of the first axial engagement element may be formed to abut the proximal inner surface 144*b*. The proximal inner surface 144*b* can guide a linear motion of the first axial engagement element 127, such that said groove on the first or second axial engagement element 127, 144*a* can become reliably engaged with the corresponding mating protrusion on the second or first axial engagement element 144*a*, 127.

Figure 11A:
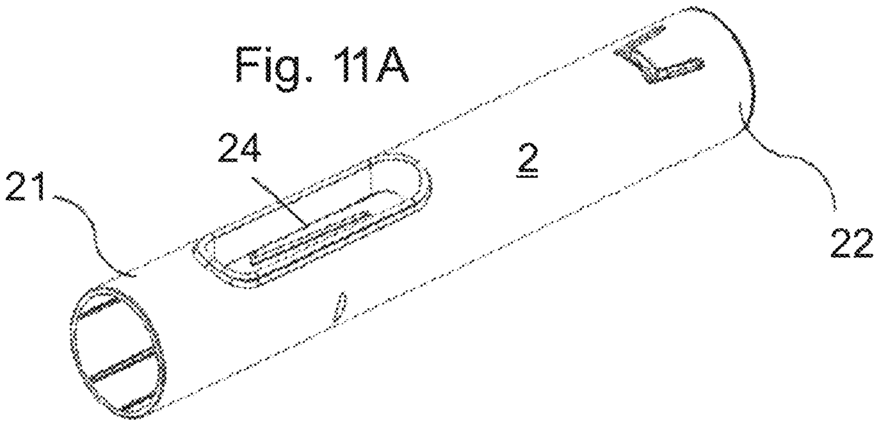
FIGS. 11A, 11B and 11C are perspective views of different components of a medicament delivery device which includes the sub-assembly according to the present disclosure.
Figure 11B:
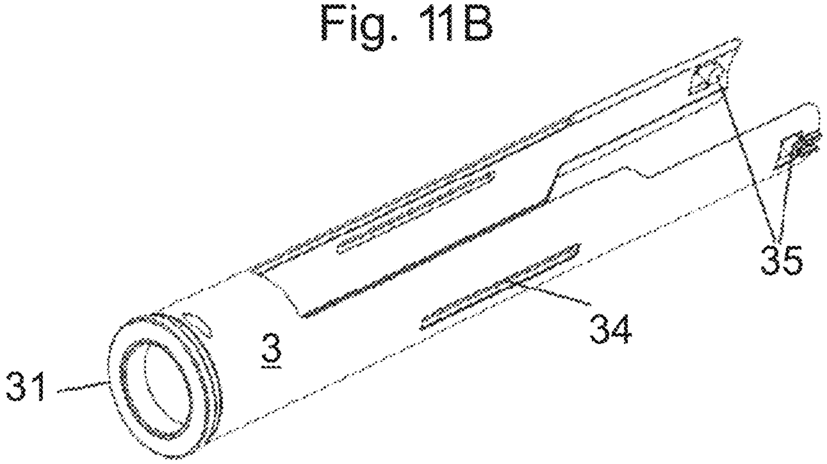
Figure 11C:
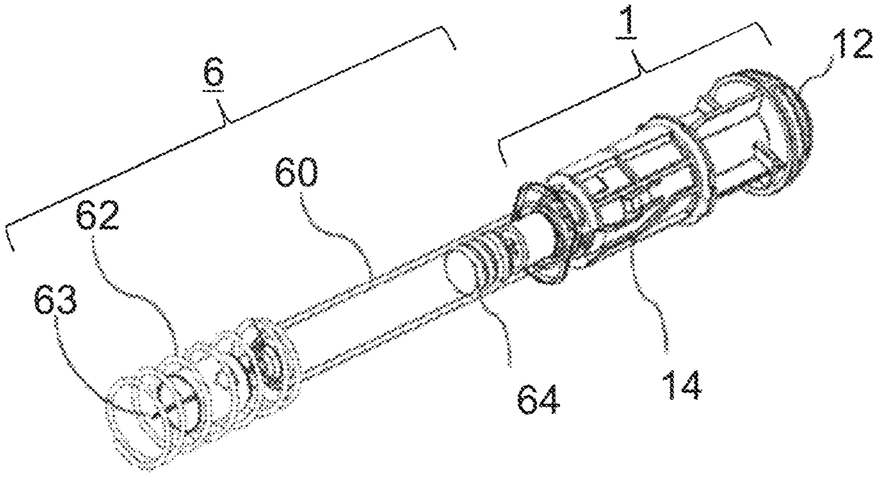

FIGS. 11A to 11C show different components assembled for the final assembly of a medicament delivery device, which includes the sub-assembly according to the present disclosure.

Specifically, FIG. 11A shows a housing 2 having a proximal end 21 and an opposite distal end 22. The housing may further comprise a protrusion (not illustrated) on its inner wall, which is adapted for receiving a recess of an activation member 3. The recess is used for locking the activation member 3 inside the housing 2, when the activation member 3 is in its most proximal position after an injection of medicament has been made. The housing 2 may further comprise a container holder 24 which is coaxially arranged and fixed attached within the housing 2 for lodging a medicament container 60.

FIG. 11B shows the activation member 3 of the medicament delivery device. The activation member 3 comprises an annular contact member 31 and a counterpart protrusion 35. In this figure, there are two counterpart protrusions 35 used for activating the medicament delivery device. The activation member 3 may comprise a guiding means 34 which is adapted to cooperate with a guiding rod (not shown) at the interior of the housing 2, for the purpose of preventing that the activation member 3 may rotate in relation to the tubular housing 2 and of allowing the activation member 3 to move in the axial direction in relation to the housing 2. Preferably, there are two guiding means 34 and correspondingly two guiding rods (not shown) used. A resilient member 62, which in an exemplary embodiment is a tension spring, is arranged at the proximal end of the activation member 3 for moving the member 3 in a proximal direction.

FIG. 11C shows the interior of the medicament delivery device comprising the sub-assembly according to the present disclosure, and a medicament releasing assembly 6. The medicament releasing assembly 6 comprises the resilient member 62 applying forces to move the activation member 3 in a proximal direction. The contact member 31 is in contact with the proximal end of the housing 2 when the medicament delivery device is in an activated state, and the contact member 31 is at a predetermined distance from the proximal end of the housing when the medicament delivery device is in a non-activated state. The medicament container 60 is arranged within the container holder 24, and has a predetermined volume of medicament, a slidable stopper 64 and a delivery member. The medicament container 60 may be a syringe provided with a needle 63 as the delivery member, but not be limited to this. Other embodiments could include a medicament cartridge having a membrane, or the like where a delivery member can be adapted. The proximal end of the plunger rod 11 is in contact with the slidable stopper 64.

In the final assembly, the sub-assembly 1 is inserted into the housing 2. An inner surface of the housing 2 and the first radial engagement element 125 interferes with each other, and thus the first radial engagement element 125 is bent radially inwards. This causes the free end portion of the first radial engagement element 125 to move or be bent slightly inwards as well. Consequently, the free end portion of the first radial engagement element 125 becomes unengaged with the recess 143. This enables rotation of the coupling member 14 relative to the main body 12 when the medicament delivery device is intentionally activated.

The rotation of the coupling member 14 to release the plunger rod 11 for injection of medicament is performed by interactions between guide channels 146, 147 longitudinally formed on an outer surface of the coupling member 14 and a counterpart protrusion 35 formed on the activation member 3.

Figure 8:
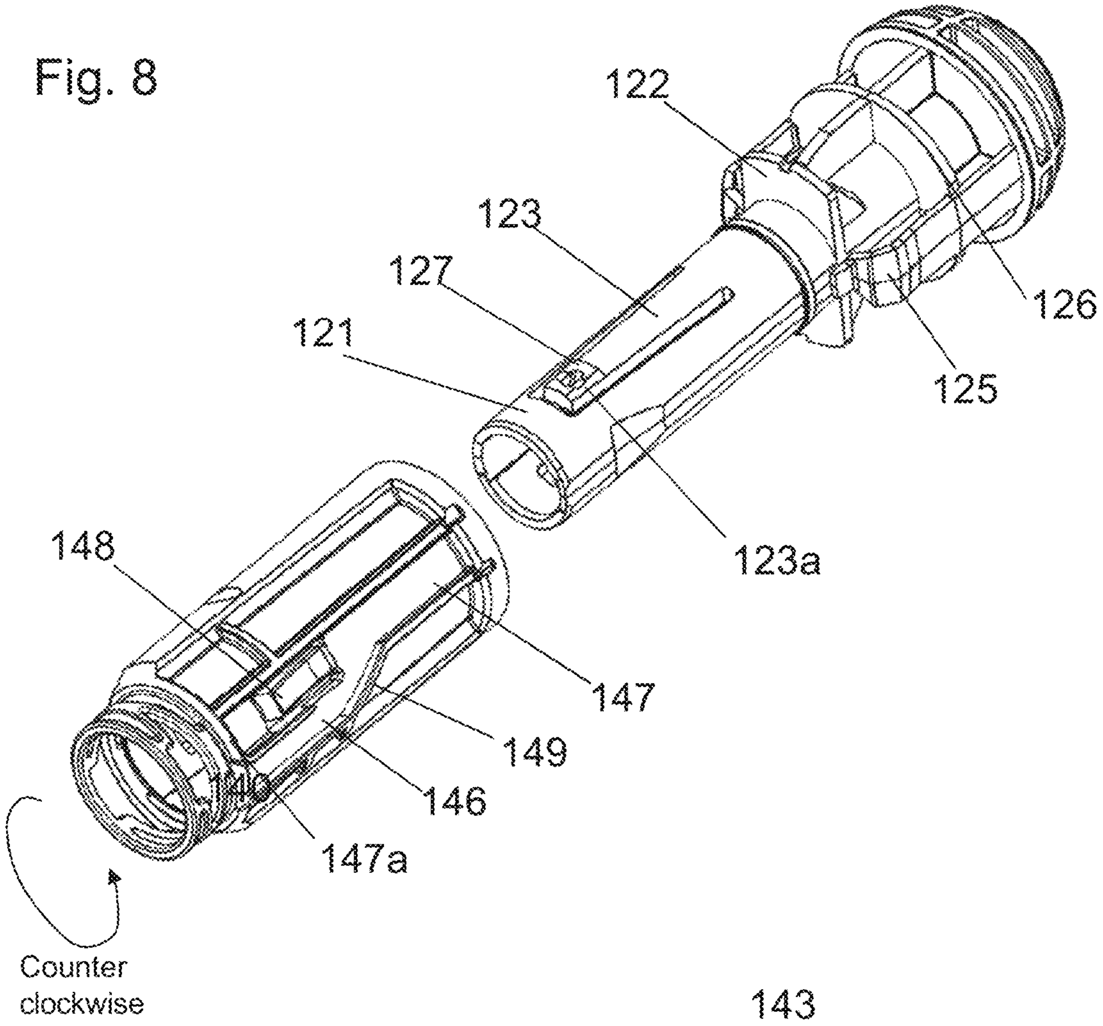
FIG. 8 is an exploded perspective view of a coupling member and a main body according to the embodiment of the present disclosure.
Figure 9:
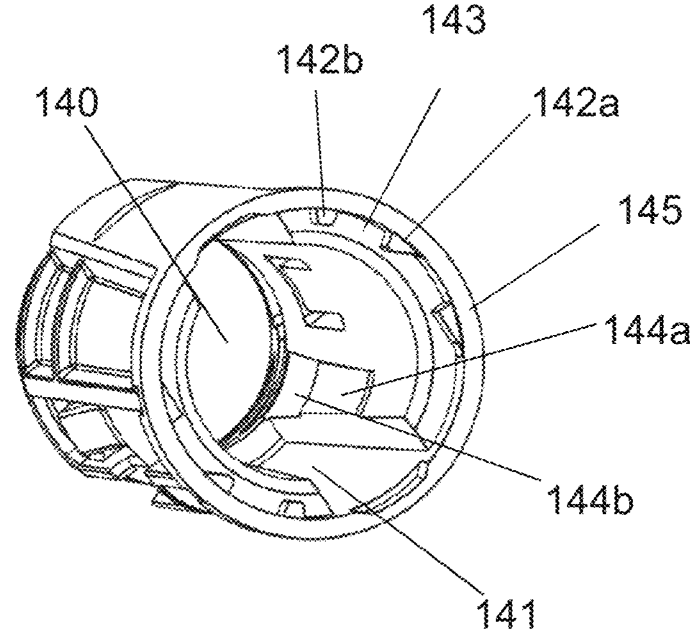
FIG. 9 is a perspective view of the coupling member according to the embodiment of the present disclosure from a different perspective angle.
Figure 10A:
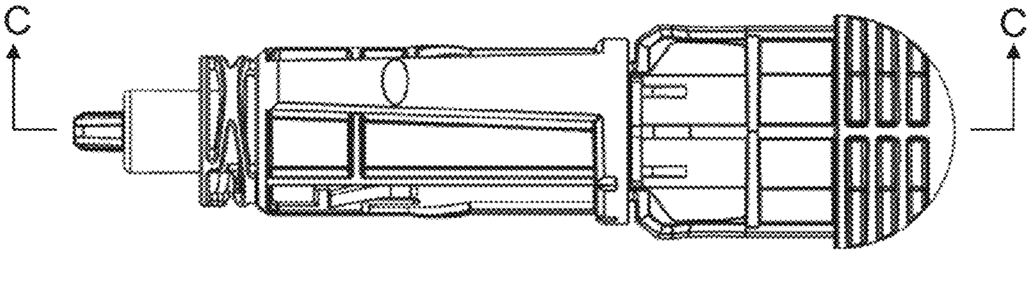
FIG. 10A is a plain side view of the sub-assembly according to the embodiment of the present disclosure.
Figure 10B:
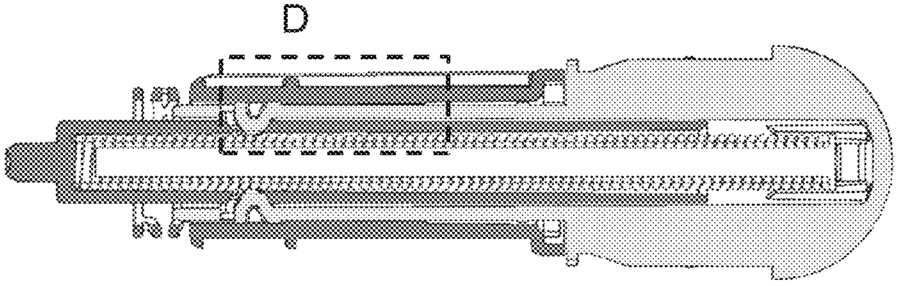
FIG. 10B is a sectional view of FIG. 10A taken along a line C-C.
Figure 10C:
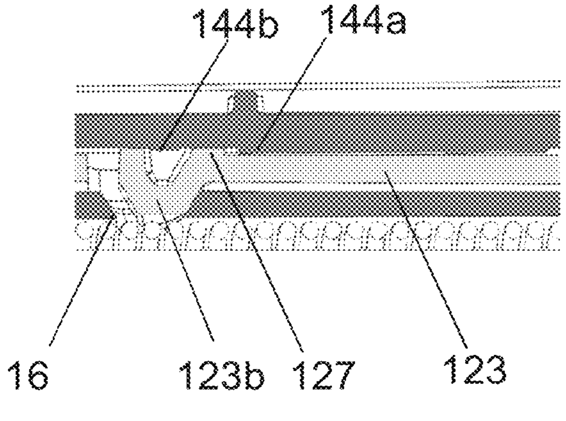
FIG. 10C is a magnifying view of a box Din FIG. 10B.

As shown in FIG. 8, the first guide channel 146 starts from the proximal end of the coupling member 14 and ends at a middle portion of the coupling member 14. The second guide channel 147 starts from the proximal end 147*a* of the coupling member 14 and substantially ends close to the distal end of the coupling member 14. The first and second guide channels 146, 147 are disposed adjacent to each other in a circumferential direction of the coupling member 14. The start of the first guide channel 146 has an opening allowing the counterpart protrusion 35 to enter, and the end of the first guide channel 146 has another opening connected to a middle part of the second guide channel 147. Further, the end of the first guide channel 146 has a slanted guide wall 149, which allows the counterpart protrusion 35 to enter the second guide channel 147. The second guide channel 147 guides the counterpart protrusion 35 to move straight toward the distal end first and then toward the proximal end of the coupling member 14. The start of the second guide channel 147 at the proximal end of the coupling member 14 is closed. A one-way stopper 148 is located adjacent to the start of the second guide channel 147, such that when the counterpart protrusion 35 becomes positioned in a channel space between the start of the second guide channel 147 and the one-way stopper 148, the counterpart protrusion 35 cannot not move in either the proximal or the distal direction.

The activation member 3 is configured to move only straight in the longitudinal direction within the housing 2, such that the counterpart protrusion 35 on the activation member 3 is so. When the activation member 3 moves straight in a distal direction, the counterpart protrusion 35 slides along the first guide channel 146 first, and is then guided toward the second guide channel 147 by the slanted guide wall 149. Since the activation member 3 is configured to move only in a straight line, the coupling member 14 gets rotated by interaction between the slanted guide wall 149 and the counterpart protrusion 35. At this point when the coupling member 14 is rotated counterclockwise, the plunger rod 11 is released.

When the activation member 3 moves back in a proximal direction by force of the resilient member 62, the counterpart protrusion 35 moves along the second guide channel 147 and then reaches the channel space between the closed end of the second guide channel 147 and the one-way stopper 148. In this state, the activation member 3 cannot move in the distal direction and covers the needle 63.

Figure 12A:
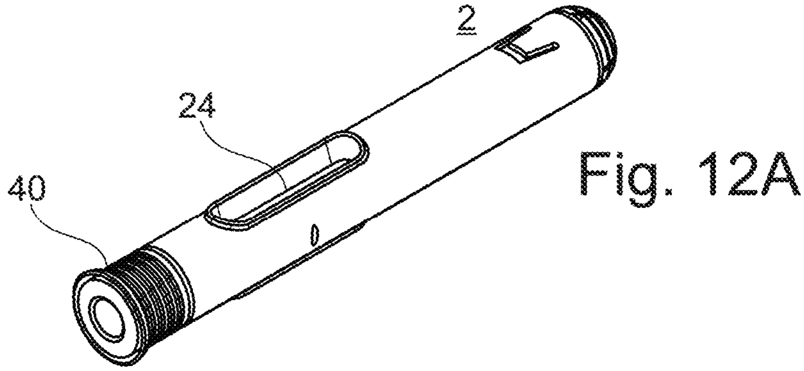
FIGS. 12A, 12B, 12C and 12D are perspective views of different states of the medicament delivery device which includes the sub-assembly according to the present invention.
Figure 12B:
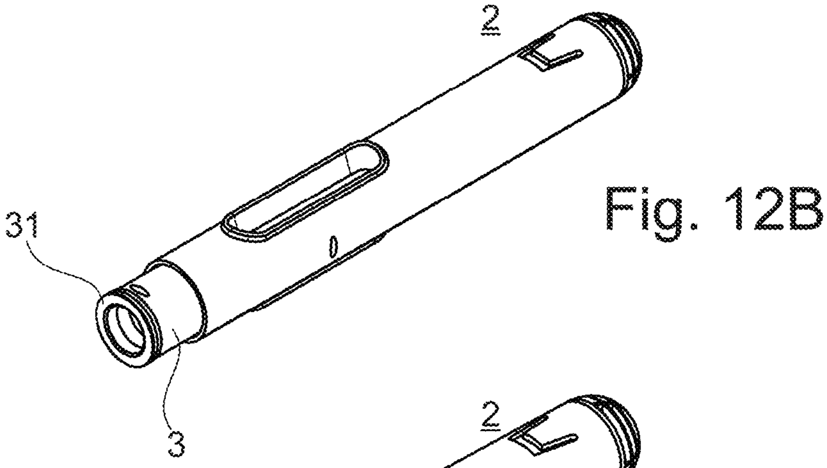
Figure 12C:
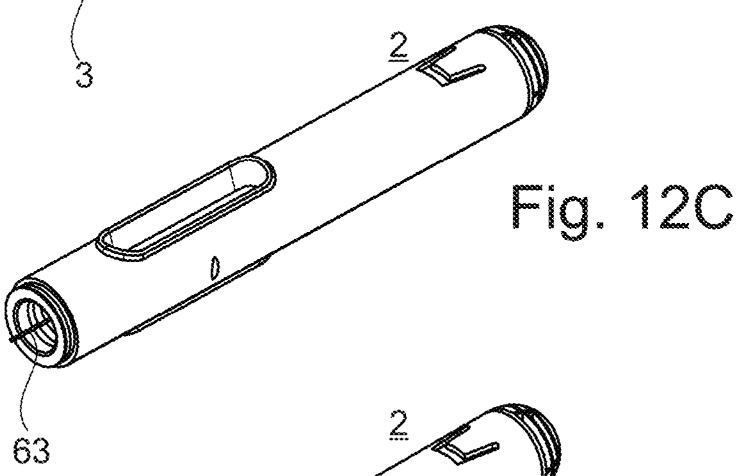
Figure 12D:
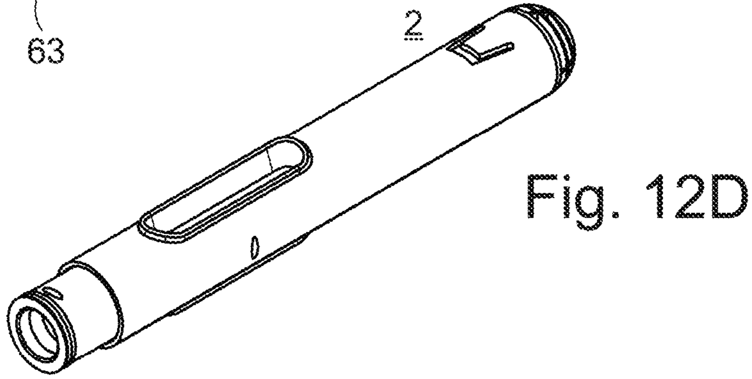

FIGS. 12A to 12D show different operation states of the medicament delivery device, which includes the sub-assembly 1 according to the present disclosure. FIG. 12A shows an initial non-activated state of the medicament delivery device having a cap 40. FIG. 12B shows an activated state of the medicament delivery device, where the cap 40 is removed. FIG. 12C shows the penetration and injection state of the medicament delivery device 1, and finally FIG. 12D shows the medicament delivery device 1 in a final locked state.

With references to FIG. 12A, the medicament delivery device comprises the housing 2, having a proximal end and an opposite distal end. The medicament injection device further comprises the activation member 3 which is slidably and coaxially arranged inside the housing 2 and comprises the contact member 31. The cap 40 is manually operated and detached just before the activation of the device.

FIG. 12B show the medicament delivery device when it is ready for use, i.e., when the device is about to perform a medicament delivery against a delivery site. The activation member 3 is then moved in the distal direction, in relation to the housing 2, and during the relative movement, a needle 63 then penetrates the skin. When the activation member 3 is about to reach its most distal position in relation to the housing 2, the medicament delivery is performed. A medicament delivery is automatically performed when the activation member 3, being in an activated position, is moved in the distal direction in relation to the housing 2.

FIG. 12C illustrates a moment when the delivery is made, and then the user removes the medicament delivery device from the delivery site. The activation member 3 moves in the proximal direction in relation to the tubular housing 2, by the force exerted by the resilient member 62 and finally reaches a final state, i.e. a locked state.

FIG. 12D illustrates the medicament delivery device in its final and locked state. The activation member 3 once more is in its most proximal position. In this state the proximal part of the activation member 3 fully protects the delivery member 63, and the activation member 3 is also locked by the engagement between the cut-out/recesses with the protrusion (not illustrated) of the housing 2, and/or by the engagement between the protrusion 35 and the one-way stopper 148. In the final position, unintentional availability of the delivery member 63 is prevented.

Various modifications to the embodiments described are possible and will occur to those skilled in the art without departing from the present disclosure which is defined by the following claims.

The invention claimed is:

1. A sub-assembly for a medicament delivery device, comprising:

a plunger rod;

a biasing member configured to bias the plunger rod;

a tubular main body comprising a hollow cylinder, wherein the plunger rod and the biasing member are in the hollow cylinder, the main body comprising a holding member attached to the hollow cylinder; and a tubular coupling member arranged to be rotatable relative to the main body, wherein the holding member is configured to have, at least, a holding position in which the holding member is engaged with the plunger rod, and a releasing position in which the holding member is released from the plunger rod, the holding member being switchable from the holding position to the releasing position depending on rotational positions of the coupling member relative to the main body, wherein the main body comprises a first axial engagement element formed on an outer surface of the holding member;

the coupling member comprises a second axial engagement element formed on an inner surface of the coupling member; and the main body and the coupling member are configured such that the first and second axial engagement elements are engaged with each other to restrict a movement of the coupling member relative to the main body in a proximal direction of the sub-assembly.

2. The sub-assembly for a medicament delivery device according to claim 1, wherein the first axial engagement element is arranged to protrude radially outwards from the outer surface of the holding member; and the second axial engagement element is arranged to protrude radially inwards from the inner surface of the coupling member.

3. The sub-assembly for a medicament delivery device according to claim 2, wherein the holding member has one end which is connected to the hollow cylinder, and another end which is a free end and capable of being engaged with the plunger rod.

4. The sub-assembly for a medicament delivery device according to claim 2, wherein the second axial engagement element is disposed between proximal and distal ends of the coupling member; and the coupling member further comprises a proximal inner surface which is disposed more proximally than the second axial engagement element, has a height difference from the second axial engagement element, and is arranged to abut the first axial engagement element.

5. The sub-assembly for a medicament delivery device according to claim 1, wherein the first axial engagement element is arranged to protrude radially outwards from the outer surface of the holding member; and the second axial engagement element comprises a groove which is formed on the inner surface of the coupling member and capable of being engaged with the first axial engagement element.

6. The sub-assembly for a medicament delivery device according to claim 5, wherein the groove is formed to extend along a circumferential direction of the coupling member or the hollow cylinder, such that the engagement between the first and second engagement elements via the groove is maintained when the coupling member is rotated relative to the main body to a certain degree.

7. The sub-assembly for a medicament delivery device according to claim 1, wherein the first axial engagement element comprises a groove which is formed on the outer surface of the holding member;

the second axial engagement element is arranged to protrude radially inwards from the inner surface of the coupling member; and the groove of the first axial engagement element is capable of being engaged with the second axial engagement element.

8. The sub-assembly for a medicament delivery device according to claim 1, wherein the coupling member has a releasing rotational position and a holding rotational position relative to the main body, which respectively correspond to the releasing position and the holding position of the holding member; and when the coupling member is in the holding rotational position, the first and second axial engagement elements are engaged with each other.

9. The sub-assembly for a medicament delivery device according to claim 1, wherein the coupling member comprises a central through-hole into which the main body can be inserted, and a longitudinal groove which can guide insertion of the main body into the coupling member; and the coupling member is rotatable relative to the main body when the main body is inserted into the coupling member along the longitudinal groove up to a pre-determined fully-inserted position.

10. The sub-assembly for a medicament delivery device according to claim 9, wherein the coupling member is in the releasing rotational position when the main body is inserted into the coupling member up to the pre-determined fully-inserted position; and the coupling member is in the holding rotational position when the coupling member is rotated in a first rotational direction by a pre-set angle from the pre-determined fully-inserted position.

11. The sub-assembly for a medicament delivery device according to claim 10, wherein the first and second axial engagement elements become engaged with each other when an external force is applied to the sub-assembly after the coupling member is rotated by said pre-set angle relative to the main body.

12. The sub-assembly for a medicament delivery device according to claim 10, wherein the first and second axial engagement elements are engaged with each other via a groove, when the position of the coupling member is changed from the releasing rotational position to the holding rotational position, or when an external force is applied to the sub-assembly after the coupling member is rotated by said pre-set angle relative to the main body.

13. A medicament delivery device, comprising:

a housing;

an activation member disposed in the housing and linearly movable along a longitudinal direction of the housing;

a medicament container disposed inside the activation member, containing medicament, and comprising a slidable stopper arranged to expel the medicament out of the medicament container, and a medicament delivery member connected with a proximal end portion of the medicament container;

a resilient member arranged to apply force to move the activation member in the proximal direction of the medicament delivery device; and the sub-assembly of claim 1, which is coupled to a distal end of the housing, arranged to push the slidable stopper when the plunger rod is released, and comprises a means of restricting a second movement of the activation member in the distal direction of the medicament delivery device after the activation member has moved in the distal direction.

14. A sub-assembly for a medicament delivery device, comprising:

a plunger rod;

a biasing member positioned inside the plunger rod;

a tubular main body comprising a proximally extending hollow cylinder configured to accept the plunger rod, where the hollow cylinder comprises a holding member; and a tubular coupling member rotatably positioned around the hollow cylinder, wherein the holding member has a holding position that is engaged with the plunger rod to axially fix the plunger rod relative to the main body, wherein the holding member has a releasing position where the plunger rod is disengaged from the holding member, wherein the holding member transitions from the holding position to the releasing position when coupling member rotates relative to the main body, wherein the holding member further comprises a first axial engagement element and the coupling member further comprises a second axial engagement element on an inner surface of the coupling member, and wherein engagement of the first and second axial engagement elements restricts the coupling member from proximal axial movement relative to the main body.

15. The sub-assembly according to claim 14, wherein the coupling member further comprises a central through-hole and a longitudinal groove which engages the hollow cylinder to guide axial insertion of the hollow cylinder into the central through-hole, where the coupling member is rotatable relative to the main body as the hollow cylinder is inserted into the central through-hole along the longitudinal groove up to a pre-determined fully-inserted position.

* * * * *